United States Patent
Tanabe et al.

(10) Patent No.: US 8,681,332 B2
(45) Date of Patent: Mar. 25, 2014

(54) METHOD OF MEASURING A DIFFUSION CHARACTERISTIC VALUE OF A PARTICLE

(71) Applicant: Olympus Corporation, Tokyo (JP)

(72) Inventors: Tetsuya Tanabe, Tokyo (JP);
Mitsushiro Yamaguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/862,021

(22) Filed: Apr. 12, 2013

(65) Prior Publication Data

US 2013/0314705 A1    Nov. 28, 2013

Related U.S. Application Data

(63) Continuation of application No. PCT/JP2011/072898, filed on Oct. 4, 2011.

(30) Foreign Application Priority Data

Oct. 13, 2010  (JP) ................................. 2010-231023

(51) Int. Cl.
*G01N 21/00* (2006.01)
*G01J 1/58* (2006.01)

(52) U.S. Cl.
USPC ........... 356/338; 356/335; 356/336; 356/337; 250/458.1; 250/459.1

(58) Field of Classification Search
USPC ................. 356/335–343, 417, 318, 319; 250/459.1, 458.1, 200, 206
See application file for complete search history.

(56) References Cited

U.S. PATENT DOCUMENTS

| 3,887,812 A | 6/1975 | Hirschfeld |
| 5,011,279 A | 4/1991 | Auweter et al. |

(Continued)

FOREIGN PATENT DOCUMENTS

| JP | 04-337446 A | 11/1992 |
| JP | 2002-507762 A | 3/2002 |

(Continued)

OTHER PUBLICATIONS

Masataka Kinjo, "Single molecule protein, nucleic acid, and enzyme assays and their procedures Single molecule detection by fluorescence correlation spectroscopy", Protein, Nucleic acid Enzyme vol. 44, No. 9, 1999, pp. 1431-1438.

(Continued)

*Primary Examiner* — Sang Nguyen
(74) *Attorney, Agent, or Firm* — Westerman, Hattori, Daniels & Adrian, LLP

(57) ABSTRACT

There is provided a method of measuring a diffusion characteristic value (for example, a diffusion constant) of a light-emitting particle using the scanning molecule counting method using the optical measurement with a confocal microscope or a multiphoton microscope. The inventive method of measuring a diffusion characteristic value of a light-emitting particle is characterized to measure light intensity from the light detection region with moving the position of the light detection region in the sample solution by changing an optical path of the optical system to generate light intensity data and to compute a diffusion characteristic value of the light-emitting particle based on a deviation time from a moving cycle time of the light detection region in an interval of generation times of two or more signals corresponding to a same light-emitting particle on the light intensity data.

7 Claims, 10 Drawing Sheets

(56) References Cited

U.S. PATENT DOCUMENTS

| | | | |
|---|---|---|---|
| 5,949,532 A * | 9/1999 | Schrof et al. | 356/73 |
| 7,330,255 B2 * | 2/2008 | Cluzel et al. | 356/318 |
| 2008/0117421 A1 * | 5/2008 | Yamaguchi et al. | 356/417 |
| 2010/0301231 A1 * | 12/2010 | Yamaguchi | 250/459.1 |
| 2012/0319009 A1 * | 12/2012 | Yamaguchi et al. | 250/459.1 |
| 2013/0048875 A1 * | 2/2013 | Yamaguchi et al. | 250/459.1 |
| 2013/0228705 A1 * | 9/2013 | Nishikawa et al. | 250/459.1 |

FOREIGN PATENT DOCUMENTS

| | | |
|---|---|---|
| JP | 2005-098876 A | 4/2005 |
| JP | 2005-164560 A | 6/2005 |
| JP | 2007-020565 A | 2/2007 |
| JP | 4023523 B2 | 12/2007 |
| JP | 2008-116440 A | 5/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2011-002415 A | 1/2011 |
| RU | 2 223 504 C1 | 2/2004 |
| WO | 98/16814 A1 | 4/1998 |
| WO | 99/47963 A1 | 9/1999 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2013/031309 A1 | 3/2013 |
| WO | 2013/031439 A1 | 3/2013 |

OTHER PUBLICATIONS

F.J. Meyer-Almes, "A new Method for Use in Molecular Diagnostics and High Throughput Pharmaceutical Screening based on Fluorescence Correlation Spectroscopy", Nanoparticle Immunoassays, R. Rigler, edit, Springer, Berlin, 2000, pp. 204-224.

Noriko Kato et al., "A single molecule analyzer that enable new analysis of DNA and protein interactions", Gene Medicine, vol. 6, No. 2, 2002, pp. 271-277.

Peet Kask et al., "Fluorescence-intensity distribution analysis and its application in biomolecular detection technology", PNAS, vol. 96, No. 24, Nov. 23, 1999, pp. 13756-13761.

Takeharu Nagai et al., "How to Measure Diffusion Coefficient of Biomolecules in Living Cells", Biophysics vol. 49, No. 4, 2009, pp. 181-186.

Masataka Kinjo et al., "Analysis of DNA structure by measurement of diffusion rate", Japanese Society of Biorheology, vol. 9, No. 2, 1995, pp. 74-83.

International Search Report of PCT/JP2011/072898, mailing date of Nov. 29, 2011.

Hebert, B et al. "Spatiotemporal Image Correlation Spectroscopy (STICS) Theory, Verification, and Application to Protein Velocity Mapping in Living CHO Cells", Biophysical Journal vol. 88, May 2005 pp. 3601-3614.

Supplemental European Search Report of Jun. 24, 2013 issued in corresponding EP application 11832447.

* cited by examiner

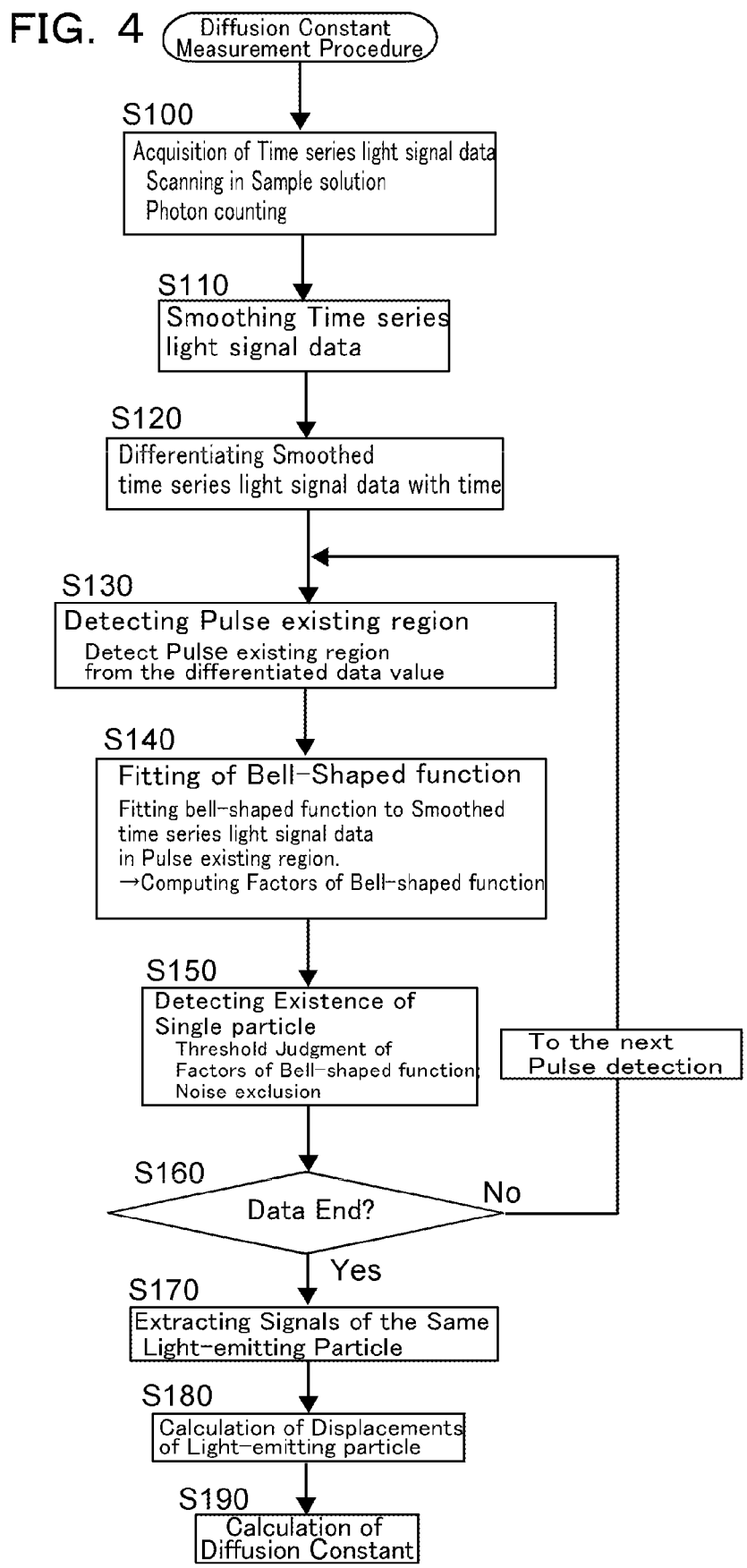

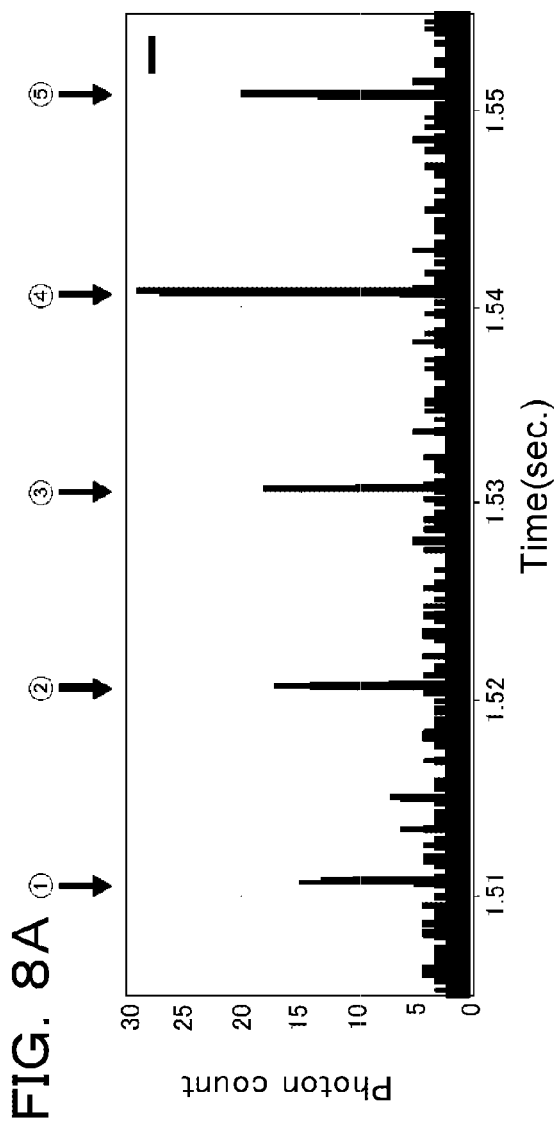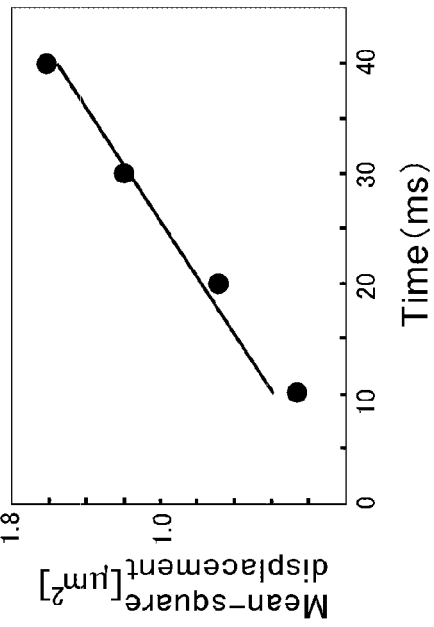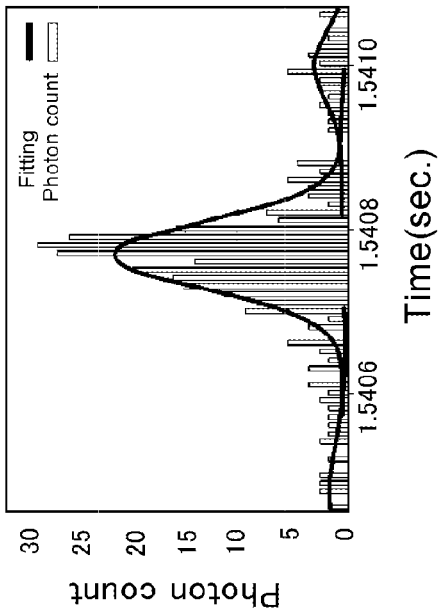
FIG. 8A
FIG. 8B
FIG. 8C

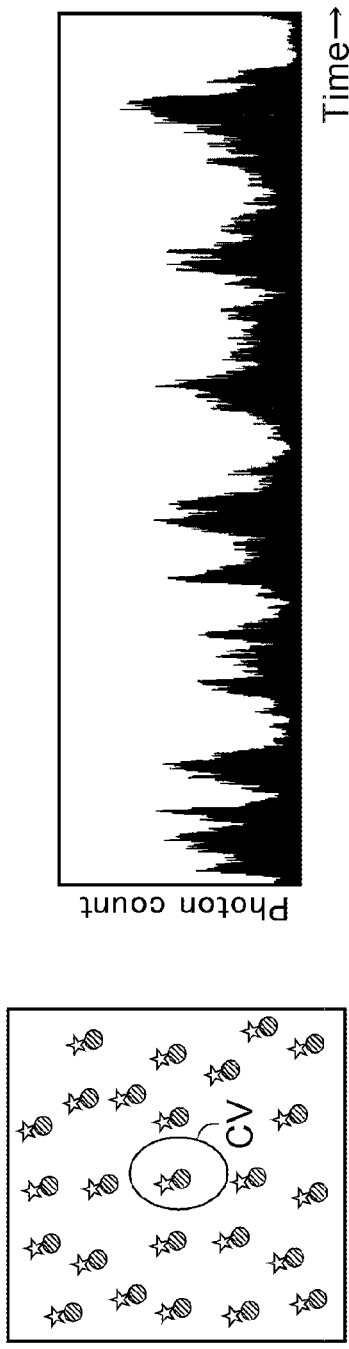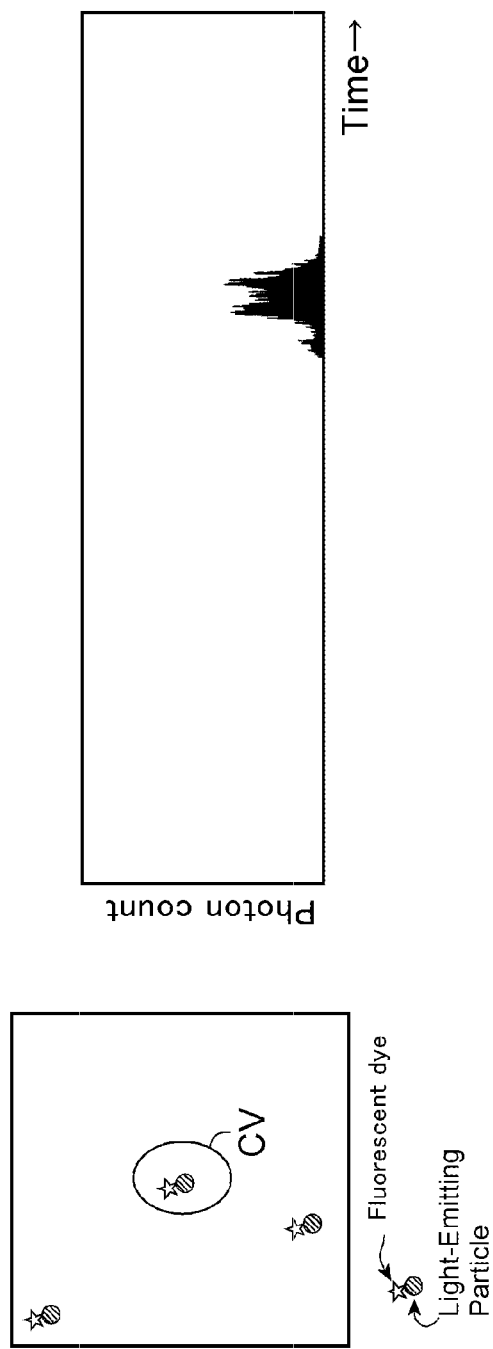
FIG. 10A High Concentration (e. g. ~ 1nM)
FIG. 10B Low Concentration (e. g. ~ 1pM)

METHOD OF MEASURING A DIFFUSION CHARACTERISTIC VALUE OF A PARTICLE

TECHNICAL FIELD

This invention relates to an optical analysis method capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a method of detecting the light from a single particle which emits light individually, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of $\mu L$), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)
Non-patent document 5: Kenji Nagai and one person, Biophysics 49 (4), 181-186 (2009)

Non-patent document 6: Masataka Kaneshiro and one person, Japanese Society of Biorheology, Vol. 9, No. 2, p 17 (1995)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light, (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

By the way, in scanning the inside of a sample solution with a light detection region in the above-mentioned scanning molecule counting method, typically, the light detection region is moved so as to circulate through a predetermined, e.g., circular or elliptical, route. In that case, when the moving cycle time of the light detection region is comparatively short or when the velocity of the diffusion translational movement of a light-emitting particle is comparatively slow, the light-emitting particle on the predetermined route hardly moves during one turn of the light detection region through the predetermined route so that the same light-emitting particle will be detected again. Actually, in a measurement of a slow moving molecule by the scanning molecule counting method, there have been observed periodic occurrences of signals indicating light of a light-emitting particle with a time interval almost equal to the moving cycle time of a light detection region (see FIG. 8A). In detailed inspections, however, it has been found that the length of the interval of the periodic signals was not completely the same as the moving cycle time of the light detection region, and also, variations between the intervals occur little by little. The variations in the lengths of the intervals of the periodic signals are considered to be caused by the positional variation of the light-emitting particle owing to the Brownian motion. The inventor of the present invention have found out that it is possible to estimate the easiness of the moving of a particle owing to the Brownian motion or the diffusion constant of a particle by analyzing the "variations" in the length of the interval of periodic signals.

Thus, the main object of the present invention is to provide a new method of measuring an index value which indicates the easiness of the moving of a light-emitting particle owing to the Brownian motion, typically, the diffusion constant of a light-emitting particle by using a detection method of a light-emitting particle of the scanning molecule counting method.

Further, another object of the present invention is to provide a method of measuring an index value which indicates the easiness of the moving of a light-emitting particle owing to the Brownian motion or a diffusion constant of a light-emitting particle in a sample solution at a lower concentration than a light-emitting particle concentration measurable in good accuracy by optical analysis techniques, such as FCS.

Solution to Problem

According to the present invention, the above-mentioned object is achieved by a method of measuring a diffusion characteristic value of a light-emitting particle dispersed and moving at random in a sample solution using an optical system of a confocal microscope or a multiphoton microscope, characterized by comprising steps of: moving periodically along a predetermined route a position of a light detection region of the optical system of the microscope in the sample solution by changing an optical path of the optical system; measuring light intensity from the light detection region with moving the position of the light detection region in the sample solution to generate light intensity data; individually detecting a signal indicating light of a light-emitting particle on the light intensity data; extracting two or more signals corresponding to a same light-emitting particle among the detected signals indicating light of the light-emitting particle; and computing a diffusion characteristic value of the light-emitting particle corresponding to the extracted signals based on a deviation time from a moving cycle time of the light detection region in an interval of generation times of the extracted signals. In this structure, "a light-emitting particle dispersed and moving at random in a sample solution" may be a particle, such as an atom, a molecule or an aggregates of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Furthermore, the "diffusion characteristic value" may be an arbitrary index value which indicates the easiness of the moving of a particle owing to the Brownian motion, and typically, it may be a diffusion constant of a particle, but it may also be the other physical quantities, such as a translational diffusion time, an arbitrary function of the diffusion constant. Further, in the followings in this specification, "a signal" means "a signal expressing light from a light-emitting particle" unless noted otherwise.

In the above-mentioned inventive method, similarly to the scanning molecule counting method, first, the measurement of light intensity is sequentially performed while the position of a light detection region is moved in the sample solution, namely, while the inside of the sample solution is scanned with the light detection region. Then, when the moving light detection region encompasses a randomly moving light-emitting particle, the light from the light-emitting particle is detected by the light detecting portion, and thereby, the existence of one particle will be detected. In this structure, in a case that the light detection region is periodically moved along a predetermined route, until the light detection region goes around the predetermined route after encompassing a certain light-emitting particle in a certain position and reaches near the position where it has encompassed the light-emitting particle, if the light-emitting particle does not deviate from the predetermined route of the light detection region, the light-emitting particle will be encompassed again in the light detection region and its light will be detected. However, the position of the light-emitting particle moves owing to the Brownian motion during the light detection region going around the predetermined route, and therefore, the interval between the first time that the light-emitting particle was detected and the next time it was detected, i.e., the interval between the generation times of the signals of the light-emitting particle is not completely equal to, but deviated from, the moving cycle time of the light detection region, and it is expected that this deviation time from the moving cycle time of the light detection region reflects the easiness of the moving of the light-emitting particle owing to the Brownian motion. Thus, in the present invention, as noted above, two or more signals which correspond to the same light-emitting particle among the detected signals indicating lights of the light-emitting particles on light intensity data are extracted, and the diffusion characteristic value of the light-emitting particle corresponding to the extracted signals is computed based on the deviation time from the moving cycle time of the light detection region in the interval between the generation times of those extracted signals. According to this structure, when a light-emitting particle enters into a predetermined route of a light detection region, its diffusion characteristic value can be individually measured, and therefore, no statistical procedures for calculation of fluorescence intensity fluctuation in optical analysis techniques, such as FCS, are required, and it is advantageous in that the diffusion characteristic value of a light-emitting particle can be obtained even when the light-emitting particle concentration in a sample solution is lower than a level necessary to obtain a good measurement result in FCS. Moreover, because a diffusion characteristic value is computed based on generation times of signals on light intensity data (one-dimensional data) according to the inventive method, it is also advantageous in that calculation load does not become so large.

In this regard, the displacement of a light-emitting particle detected by the above-mentioned method is computed from the deviation time from the cycle time of a light detection region in the interval of generation times of signals extracted as signals of the same light-emitting particle on light intensity data and the moving speed of the light detection region. Thus, in calculation of the above-mentioned diffusion characteristic value, the displacement of a light-emitting particle may be computed first, and, based on the displacement of the light-emitting particle, the diffusion characteristic value of the light-emitting particle may be computed. In particular, from the displacement x of a particle in a certain time t, the diffusion constant D is defined by:

$$<x(t)>^2 = 2Dt \quad (1)$$

(where $<x(t)>$ is the average of displacements), and thus, it may be computed based on the displacement of the light-emitting particle, using the relation of the Expression (1).

Further, it should be understood that the interval of generation times of signals extracted as signals of the same light-emitting particle on light intensity data may not always be the difference between the generation times of the signals adjoining in time but the time difference between generation times of any two signals in the two or more continuous, extracted signals. For instance, when n signals are extracted as signals of the same light-emitting particle, the intervals of generation times of two signals of all the combinations of two in the n signals may be used for calculation of a diffusion characteristic value or a diffusion constant. That is, when n signals are extracted, n(n−1)/2 of the interval values between generation times of signals are obtained, and a diffusion characteristic value or a diffusion constant may be computed using the values of those generation time intervals. According to this way, it is advantageous in that much displacement values will be obtained in a short measuring time and a reliable calculating result is obtained as compared with a case that a displacement of a particle is measured subsequently from the difference between generation times of adjoining signals.

Furthermore, in the step of extracting two or more signals corresponding to the same light-emitting particle from the signals on the above-mentioned light intensity data, a signal generated within a time width, determined based on the size and moving speed of the light detection region, from the time obtained by adding the cycle time of the light detection region to a generation time of one signal among detected signals indicating lights of light-emitting particles may be judged as a signal of the same light-emitting particle as the light-emitting particle corresponding to the above-mentioned one signal. As noted above, in the inventive method, the same light-emitting particle is detected periodically each time the light detection region has circulated through a predetermined route (not by pursuing one light-emitting particle continuously), and a diffusion characteristic value or a diffusion constant is computed from the interval or displacement of generation times of the signals. Thus, in the time (cycle time) of the circulation of the light detection region, when a diffusion characteristic value or a diffusion constant is so large that the (average) displacement of the light-emitting particle exceeds beyond the size of the light detection region, it is possible that the signal of the same light-emitting particle cannot be periodically detected. That is, conversely, when the displacement of the light-emitting particle in the time of a circulation of the light detection region is smaller than the size of the light detection region, the interval of the signals of the light-emitting particle becomes within the range of the value given by adding to, or subtracting from, the cycle time of the light detection region a half of the time width taken for the light detection region to move the size of the light detection region. And, the time width taken for the light detection region to move the size of the light detection region is determined based on the size and moving speed of the light detection region, and therefore, after all, it is considered that a certain signal, and another signal which has been generated within the range of the value given by adding to, or subtracting from, the cycle time of the light detection region a half of the time width determined based on the size and moving speed of the light detection region from the generation of the certain signal, are the signals of the same light-emitting particle. Thus, as noted above, in accordance with the manner that a signal generated within the time width determined based on the size and moving speed of the light detection region in which the time given by adding the cycle time of the light detection region to the generation time of one signal is centered is judged as a signal of the same light-emitting particle as the light-emitting particle corresponding to the above-mentioned one signal, it becomes possible to extract the signals of the same light-emitting particle. Concretely, the time width ΔT determined based on the size and moving speed of the light detection region may be given with the diameter d and moving speed v of the light detection region by:

$$\Delta T = d/v \qquad (2).$$

Moreover, in the inventive method, in a case that signals indicating lights from two or more light-emitting particles are present on a light intensity data, a diffusion characteristic value or diffusion constant may be independently computed for each of those two or more light-emitting particles. According to the inventive method, when two or more light-emitting particles exist on a predetermined route during the circulation of a light detection region through the route, those are detected independently. Accordingly, by extracting the signals of those light-emitting particles for the respective light-emitting particles, diffusion characteristic values or diffusion constants can be computed for the respective ones. According to this structure, it is advantageous in that diffusion characteristic values or diffusion constants of two or more light-emitting particles on one light intensity data can be obtained, and many results are obtained in a short measuring time.

With respect to the step of moving the position of the light detection region in the above-mentioned inventive structure, the moving speed of the position of the light detection region in the sample solution is appropriately changed based on the characteristic or the number density or concentration of the light-emitting particle in the sample solution. As understood by ones skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the above-mentioned step of moving the position of the light detection region, the moving speed of the position of the light detection region in the sample solution is preferably set to be higher than the diffusional moving velocity of a light-emitting particle (the average moving speed of a particle owing to the Brownian motion). As explained above, in the inventive method, a light-emitting particle will be detected individually by detecting the light emitted from the light-emitting particle encompassed by the light detection region. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal (during one circulation of the light detection region through a predetermined route). In this regard, since the diffusional moving velocity differs depending upon light-emitting particles, it is preferable that the moving speed of the light detection region can be changed appropriately according to the characteristics (especially, the diffusion characteristic value or diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement route of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow. Moreover, the calculation of a diffusion constant from the displacement of a particle in flowing liquid is complicated.). Further, since no structure for flowing a sample solution is required, the measurement and analysis can be conducted with a small amount of the sample solution (at the level of one to several tens of μL) similarly to FCS and FIDA, etc.

The inventive method is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, according to the inventive method, as well as detecting an existence of a light-emitting particle individually by scanning the inside of a sample solution with a light detection region in a confocal microscope or a multiphoton microscope, the measurement of a diffusion characteristic value or a diffusion constant of the light-emitting particle becomes possible. And, the diffusion characteristic value or diffusion constant reflects the size and shape of the particle, and therefore, in accordance with the measurement by the inventive method, the identification of a particle, the detection of the size, shape their changes of a particle, or the detection and analysis of various phenomena, such as a binding and dissociation reaction or dispersion and aggregation of particles becomes possible.

The measurement of a diffusion characteristic value or a diffusion constant in the above-mentioned inventive method is based on a new principle, having some features different from the conventional measurement or estimating method of a diffusion constant. For example, according to FCS, the translational diffusion time of a light-emitting particle dispersed and moving at random in a sample solution is computed and it is possible to estimate a diffusion constant of the light-emitting particle from the translational diffusion time; however, the translational diffusion time of FCS is a value obtained from an autocorrelation function of the fluorescence intensity in a measuring time which has been computed, and the diffusion constant computed therefrom is the average value of many light-emitting particles in a sample solution. Thus, in a case that different kinds of light-emitting particle are present in a sample solution, an operation processing becomes complicated, and for example, when light-emitting probes is attached to particles to be observation objects, and measurements by FCS are carried out for the particles, any purification treatments for removing light-emitting probes having not bound to the particle to be detected may be needed. Moreover, as already noted, for calculating an autocorrelation function of fluorescence intensity in good precision by FCS, the light-emitting particle concentration in a sample solution needs to be a level at which one or more light-emitting particle(s) always exist(s) in the measuring time. On the other hand, according to the inventive method, it is possible to compute the individual diffusion characteristic value or diffusion constant of a particle by detecting an existence of the particle and its position individually. Thus, the light-emitting particle concentration in the sample solution at which the measurement can be performed in good precision may be significantly lower than the case of FCS, and in a case that kinds of light-emitting particle can be discriminated with signal characteristics, etc., whether or not different kinds of light-emitting particle are present in a sample solution seldom influences the difficulty in calculation of a diffusion characteristic value or a diffusion constant, and thus, it is advantageous in that the removal of the light-emitting probes are not necessary even in a case of the measuring of particles to which light-emitting probes have been attached.

Further, as other examples in the conventional technologies enabling the computation of a diffusion constant of a particle, according to SMT (Single Molecule tracking) or RICS (Raster Imaging Correlation Spectroscopy) (non-patent document 5), it is possible to pursue the Brownian motion of a light-emitting particle in a solution on the images captured under the light microscope, and to estimate a diffusion constant from the two-dimensional motion of the particle, however, in those cases, the analysis of two-dimensional data (image data) is required, and also it is difficult to catch a quick motion of the light-emitting particle (For example, the time resolution of the displacement of a particle is subject to a restriction with a video rate). On the other hand, in the inventive method, a diffusion characteristic value or a diffusion constant is computed using one-dimensional data (time series light intensity data), and accordingly, the operational load is lighter than the analysis operation of image data, and also, by adjusting appropriately the moving speed and/or route length of the light detection region, the diffusion constant of a quickly moving particle (as compared with the cases of SMT and RICS) can be measured individually for each light-emitting particle.

Thus, according to the way of detecting a light-emitting particle individually and computing individually its diffusion characteristic value or diffusion constant in accordance with the inventive method, as noted above, there are obtained some advantages which are not seen in conventional measurement or estimating methods of a diffusion characteristic value or a diffusion constant. Especially, in this invention, since a light-emitting particle is detected individually, a light-emitting particle is detectable even at relatively low concentration in a sample solution so that its light would be buried in the light from other light-emitting particles in the conventional method, and the diffusion characteristic value or diffusion constant thereof becomes measurable.

Other purposes and advantages of the present inventions will become clear by explanations of the following preferable embodiments of the present invention.

BRIEF DESCRIPTIONS OF DRAWINGS

FIG. 1A is a schematic diagram of the internal structure of an optical analysis device with which the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method which constitutes a part of the inventive method, respectively.

FIGS. 3A through 3D are drawings explaining the principle of measurement of a diffusion constant of a light-emitting particle according to the inventive method. FIG. 3A is a typical perspective diagram of the spatial domain encompassed by the moving of a light detection region CV of a microscope along a predetermined route in a sample solution. FIG. 3B is a graph chart which schematically shows the light intensity from a light-emitting particle detected when a light detection region circulates through a predetermined route and a light-emitting particle hardly moves against time. FIG. 3C is typical perspective diagrams of a spatial region passed by a light detection region CV which circulates through a predetermined route, showing the relation of the moving length of a light-emitting particle and the times when the light-emitting particle is detected. FIG. 3D is a schematic diagram of a light detection region explaining the relation between the size of the light detection region and the displacement (per cycle time of the light detection region) of the light-emitting particle owing to the Brownian motion measured by the inventive method.

FIG. 4 is a drawing showing in the form of a flow chart the procedures of a diffusion constant measurement performed in accordance with the inventive method.

Figure 6A:
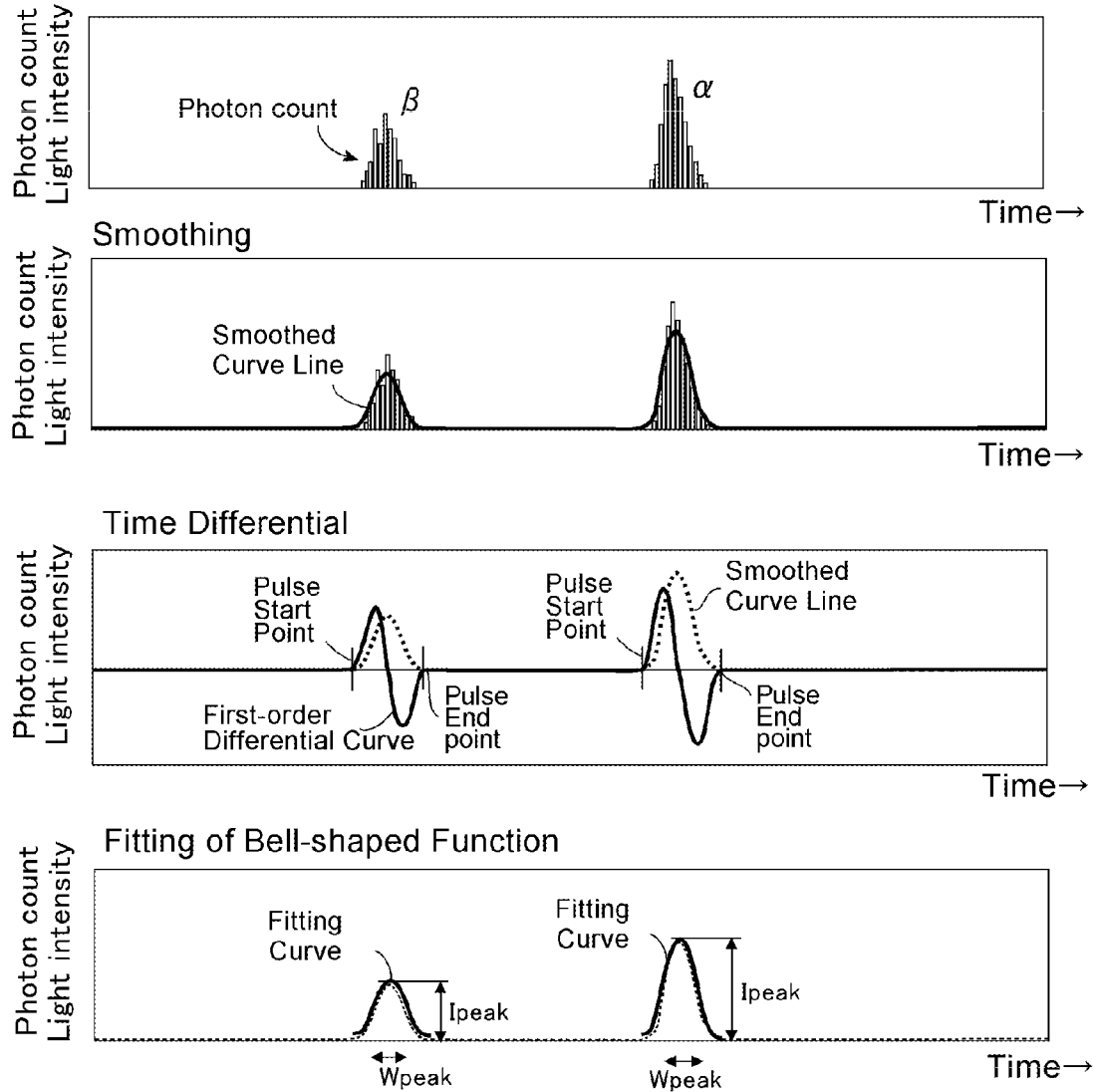
Figure 6B:
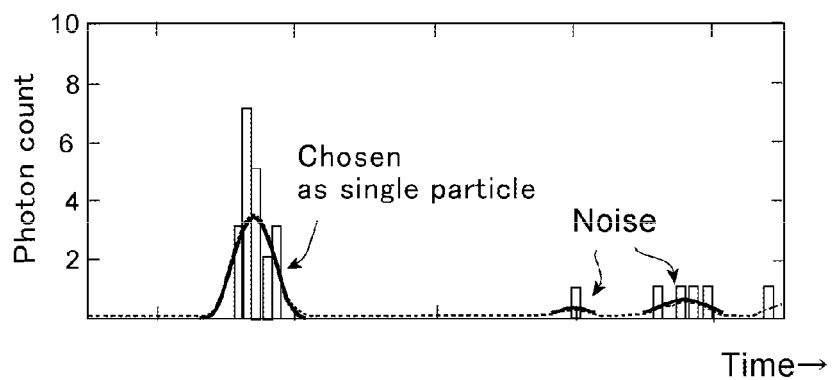

FIG. 6A is drawings explaining an example of the signal processing step of the detected signals in the procedure for detecting the existence of a light-emitting particle from the measured time series light intensity data (change in time of photon count) in accordance with the scanning molecule counting method. FIG. 6B shows examples of measured photon count data (bar graph); curves obtained by carrying out the smoothing of the data (dotted line); and gauss functions fitted on the pulse existing region (solid line). In the drawing, the signals attached with "noise" are disregarded as signals due to noises or a contaminant.

Figure 7A:
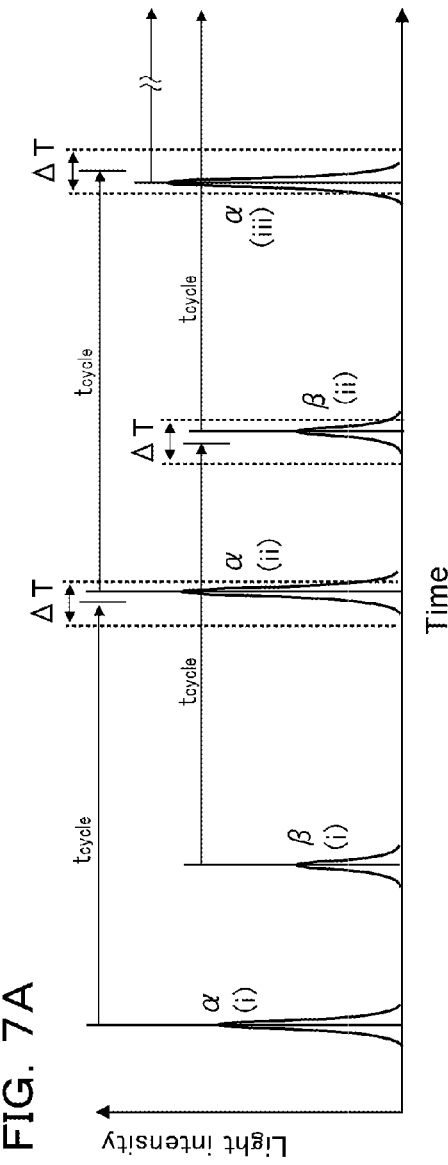
Figure 7C:
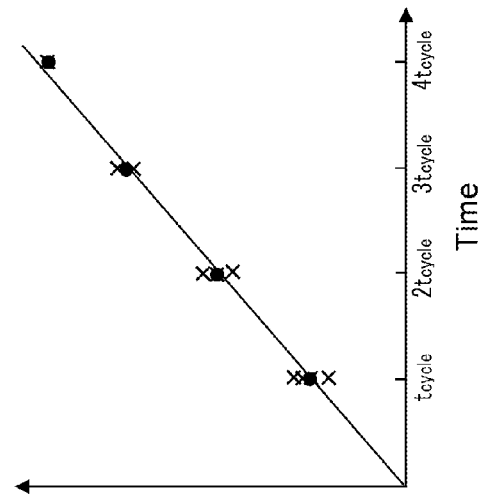
Figure 7B:
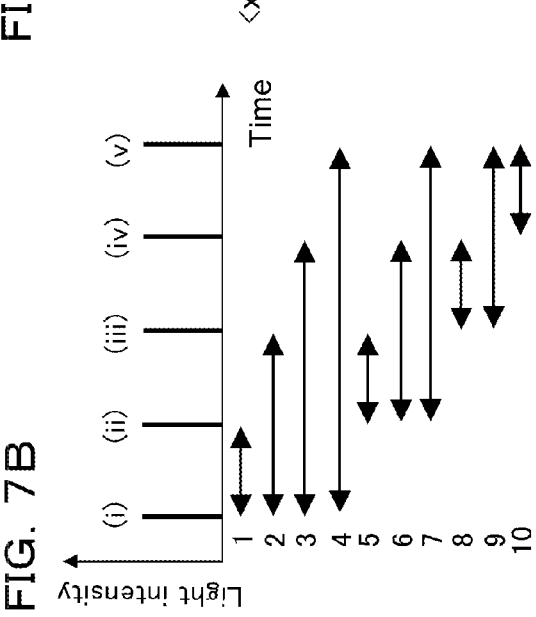

FIG. 7A is a diagram explaining one example of a process which extracts signals of the same light-emitting particle (α or β) among the signals of light-emitting particles detected on time series light intensity data. FIG. 7B is a diagram explaining generation time intervals of signals seen in the extracted signals ((i)-(v)) of the same light-emitting particle. FIG. 7C is a schematic graph chart showing plots of the mean-square displacements of a light-emitting particle, determined based on the deviation times from the moving cycle time of the light detection region in the generation time intervals of the signals, against time (when the displacement occurred) and the fitting line to the plots. (The gradient of the fitting line is a function (=2D) of the diffusion constant D of the light-emitting particle.)

FIG. 8A shows an observation example of time series light intensity data (photon count data) in which periodic, strong pulse form signals were observed in Embodiment 1, and FIG. 8B shows the photon count data of the signal 4, enlarged in the time direction, and its fitting curve. FIG. 8C is a graph chart showing plots of the mean-square displacements of a light-emitting particle computed based on deviation times from the moving cycle time of a light detection region in the intervals of generation times of signals in FIG. 8A against time (the number of cycles×moving cycle time) and its fitting line.

Figure 9:
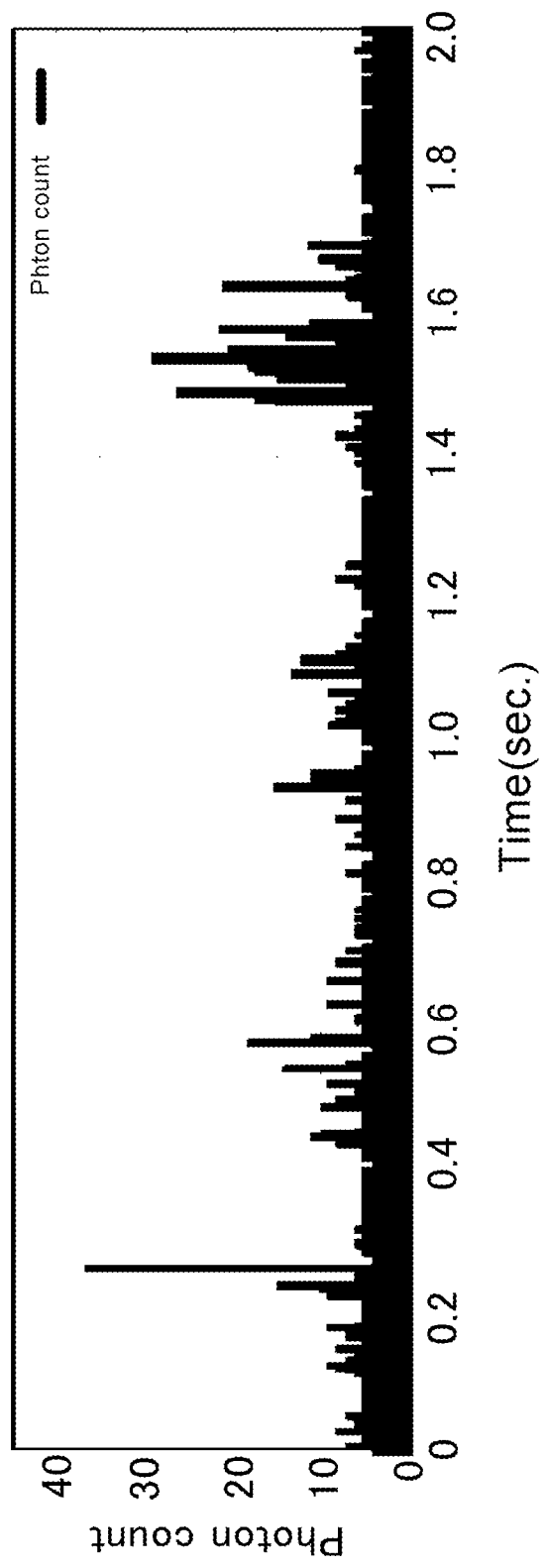

FIG. 9 shows the whole time series light intensity data (photon count data) (for 2 seconds) measured in Embodiment 1.

FIGS. 10A and 10B show examples of the time variation of the photon count (light intensity) obtained in a conventional optical analysis technique computing fluorescence intensity fluctuation, where FIG. 10A shows a case that the particle concentration is at a level providing a sufficient precision in the measurement, and FIG. 10B shows a case that the particle concentration in a sample is significantly lower than the case of FIG. 10A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

Figures 1A, 1B, 1C:
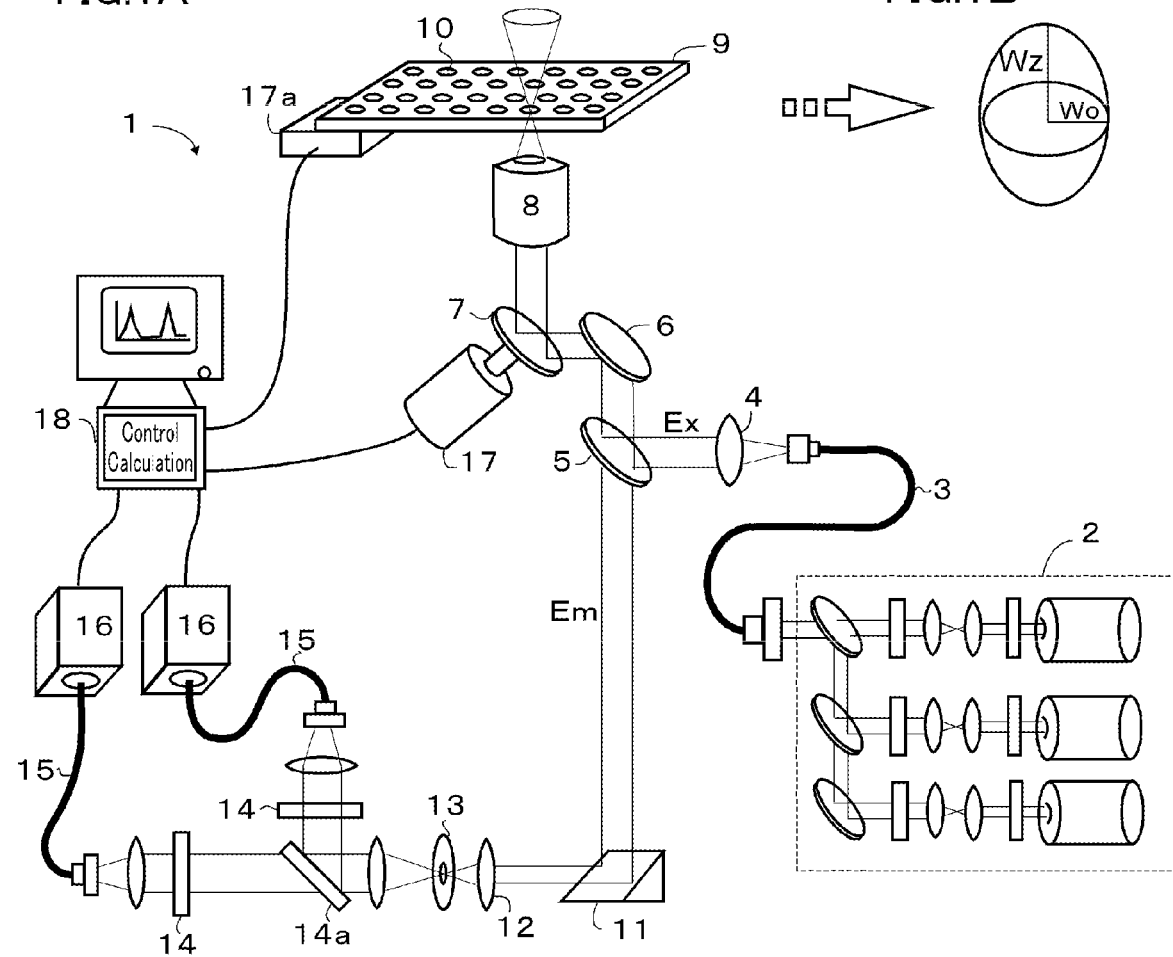

In the basic structure, the method according to the present invention can be realized with an optical analysis device constructed by associating the optical system of a confocal microscope and a photodetector, enabling FCS, FIDA, etc., as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as a "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity reduced to $1/e^2$ of the peak intensity. Then, the light having passed through the pinhole 13 passes through the dichroic mirror 14a and transmits through the corresponding barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. For the photodetector 16, preferably, a super high sensitive photodetector, usable for the photon counting, is used, so that the light from one light-emitting particle, for example, the faint light from one or several fluorescent dye molecule(s), can be detected.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement route of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence or scattered light, the above-mentioned optical system of the confocal microscope is used as it is. Further, in the case that a light-emitting particle emits light owing to a chemiluminescence or bioluminescence phenomenon without excitation light, the optical system 2-5 for generating excitation light may be omitted. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may also be provided so as to detect the lights from light-emitting particles of two or more kinds having different light-emitting wavelengths, if contained in a sample, separately depending upon the wavelengths.

The Principle of the Inventive Method

As described in the column of "Summary of Invention", according to the inventive method, briefly, in the "scanning molecule counting method" which detects individually an existence of a light-emitting particle dispersed in a sample solution by detecting light emitted by the light-emitting particle when it is encompassed in a light detection region of a confocal microscope or a multiphoton microscope during the periodic moving of the position of the light detection region through a predetermined route within the sample solution, there is computed the easiness of the moving of the light-emitting particle, i.e., the diffusion characteristic value or the diffusion constant of the light-emitting particle based on the deviation times from the moving cycle time of the light detection region in the intervals of generation times of signals of the light-emitting particle reflecting the displacements of the position of the light-emitting particle during the circulation of the light detection region through the predetermined route. According to this structure, each of the light-emitting particles in the sample solution is detected individually and its diffusion characteristic value or diffusion constant is measured individually, and therefore, even when the light-emitting particle concentration in the sample solution is lower than the concentration well measurable in spectral analysis techniques, such as FCS, etc., which require a statistical procedure for calculation of the magnitude of fluorescence fluctuation, a measurement of the diffusion characteristic value or diffusion constant of the light-emitting particle becomes possible. In the following, the principles of the scanning molecule counting method and the measuring method of a diffusion characteristic value or a diffusion constant in accordance with the present invention are described.

1. Principle of Scanning Molecule Counting Method

Spectral analysis techniques, such as FCS, etc., are advantageous in that the required sample amount is extremely small and a test can be performed promptly as compared with the conventional biochemical analytical techniques. However, in these spectral analysis techniques such as FCS, etc., the characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 10A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn in FIG. 10B, no significant light intensity signal (photon count) would appear in a part of the measuring term as illustrated in the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring term should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its concentration, even when the concentration of the light-emitting particle is lower than the level requested in the above-mentioned spectral analysis techniques, such as FCS and FIDA.

Figure 2A:
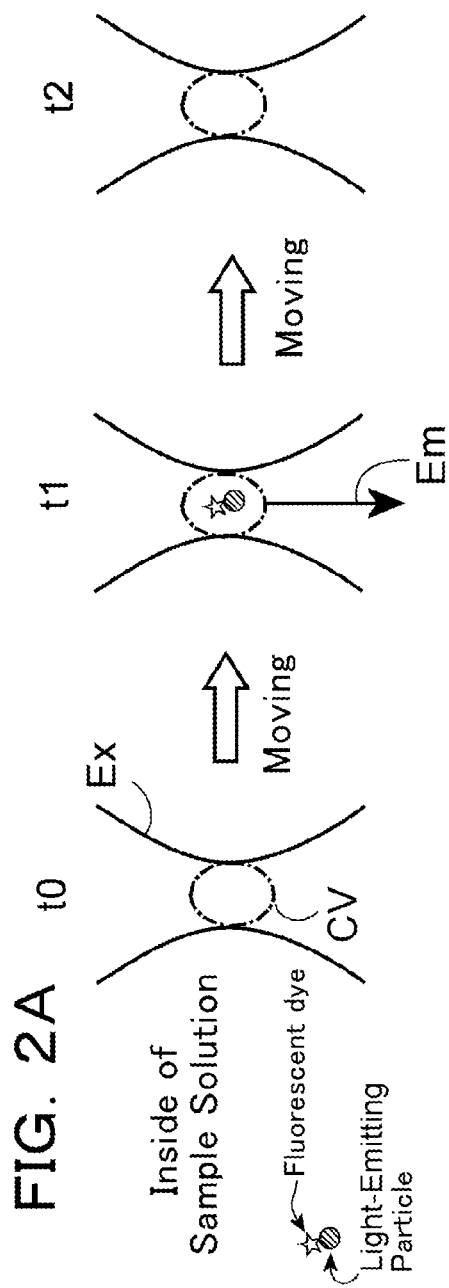
Figure 2B:
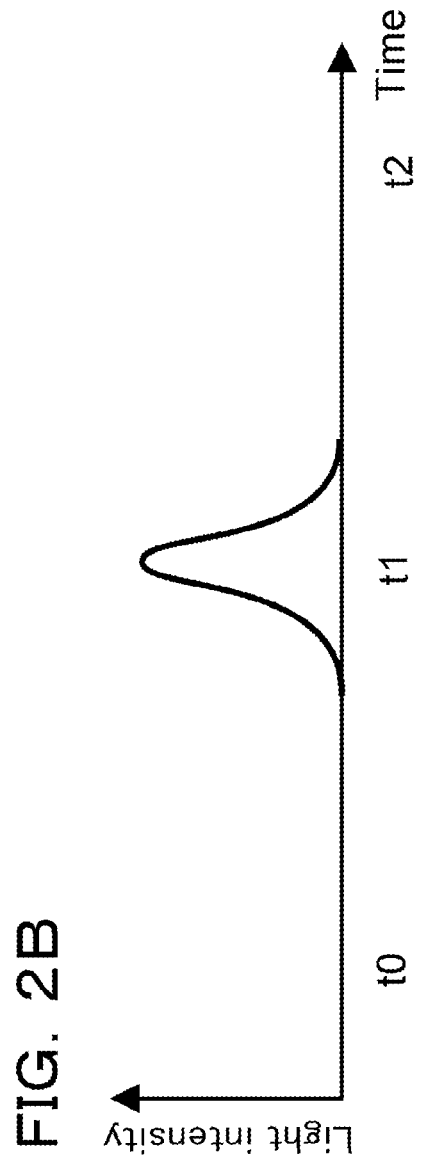

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particle is detected individually, and the information about a characteristic of the light-emitting particle can be acquired. In the principle of the scanning molecule counting method, no statistical calculation processes, such as the calculation of the fluorescence intensity fluctuation, are conducted and a light-emitting particle is one by one detected, and therefore, the information about a characteristic of the particle is acquirable even in a sample solution with a low particle concentration at the level where no sufficiently accurate analysis is available in FCS, FIDA, etc.

Figure 3A:
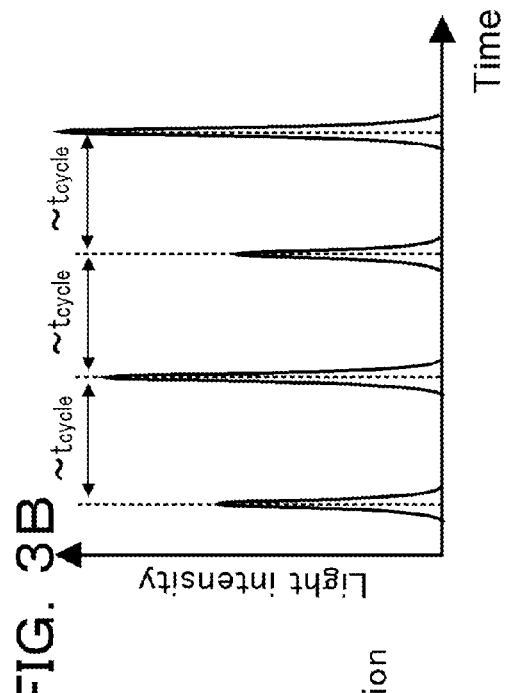
Figure 3B:
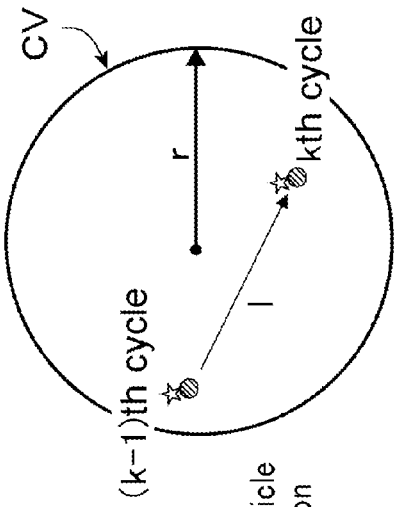

2. Principle of Measurement of Diffusion Characteristic Value of Light-Emitting Particle According to the Present Invention In the above-mentioned scanning molecule counting method, as schematically drawn in FIG. 3A, a light detection region (CV) is made circulate so as to pass through a predetermined route (for example, a ring of radius R) in a sample solution. During this movement of the light detection region, the position of a light-emitting particle moves owing to the Brownian motion, and when a light-emitting particle detected once (a light-emitting particle once encompassed in the light detection region) does not deviate from the spatial region through which the light detection region passes during the circulation of the light detection region through the predetermined route, this light-emitting particle will be detected again. Especially when the speed of the Brownian motion of the light-emitting particle is comparatively low, the light-emitting particle detected once will be encompassed in the light detection region at each circulation of the light detection region in a certain term, and accordingly, on light intensity data, as schematically illustrated in FIG. 3B, signals indicating light of the light-emitting particle are periodically detected almost by the time (moving cycle time) tcycle of one circulation of the light detection region through the predetermined route. However, the intervals of generation times of periodically detected signals are not completely equal to the moving cycle time of the light detection region, and increases and/or decreases relative to the moving cycle time of the light detection region depending on the movement of the position of the light-emitting particle owing to the Brownian motion during the moving of the light detection region through the predetermined route, namely, the deviation time from the moving cycle time is generated. Then, in the present invention, based on the above-mentioned deviation time from the moving cycle time of a light detection region in the intervals of generation times of periodically detected signals, it is tried to compute out the moving easiness owing to the Brownian motion i.e., a diffusion characteristic value of a light-emitting particle. In this regard, although, in the followings, the example of computing a diffusion constant as a diffusion characteristic value is explained, it should be understood that other diffusion characteristic values are computable appropriately based on the deviation times from the moving cycle time in the intervals of generation times of signals, also, and such a case belongs to the scope of the present invention.

Figure 3C:
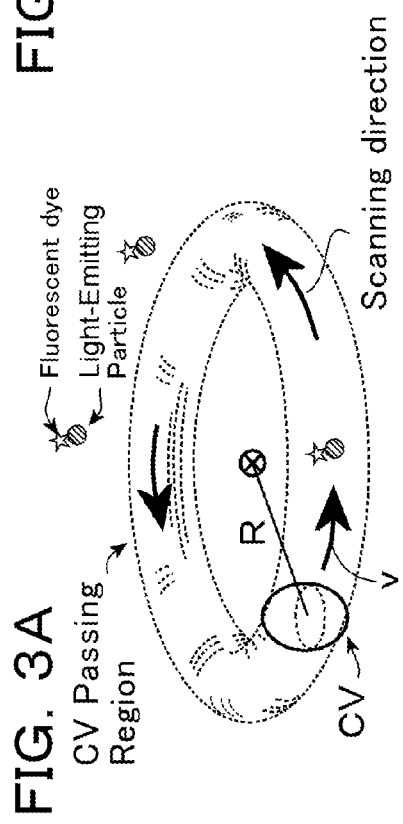

Concretely, the generation times of periodically detected signals of a light-emitting particle and the diffusion constant of the light-emitting particle are associated with one another as in the following. First, as shown in the left of FIG. 3C, when, after a light-emitting particle is encompassed ay time t=to in a light detection region and a signal of the light-emitting particle is generated, the light detection region circulates through a predetermined route k times (k is a positive integer) with the moving cycle time tcycle to encompass the same light-emitting particle, whereby the signals are detected, the position of the light-emitting particle moves as shown in the right of FIG. 3C, and accordingly, the generation time t=tk of the signal is given by:

$$t = tk = to + k \cdot tcycle + \Delta t \quad (3)$$

Here, $\Delta t$ is the difference of the times of encompassing the light-emitting particle in the light detection region owing to the moving of the position of the light-emitting particle, namely, the deviation time from the moving cycle time of the light detection region in the interval of the generation times of two signals ($\Delta t$ may be positive or negative.). Thus, the displacement $x(k \cdot tcycle)$ of the position of the light-emitting particle along the moving direction of the light detection region in $k \cdot tcycle$ (k cycle times) is given with the moving speed v of the light detection region, by:

$$x(k \cdot tcycle) = v \Delta t \quad (4).$$

By the way, in accordance with the Einstein-Smoluchowski equation, the relation between the diffusion constant D of a particle and one-dimensional displacement x (t) of the particle in time t is given by:

$$<x(t)>^2 = 2Dt \quad (5)$$

Thus, using Expressions (3) and (4), from the deviation times from the moving cycle time of the light detection region in the intervals of the generation times of the periodically detected signals, the displacements $x(k \cdot tcycle)$ of the position of the light-emitting particle are computed, and using those displacement, it becomes possible to compute the diffusion constant D with Expression (5).

Figure 3D:
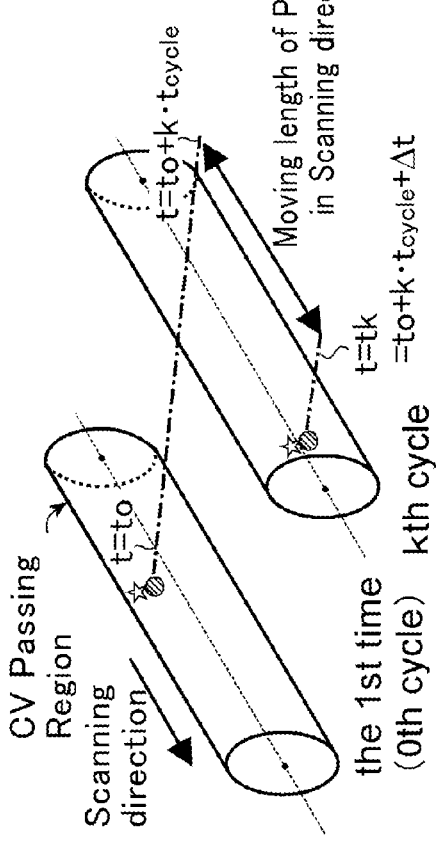

By the way, in a case that a diffusion constant is so large that the (average) displacement of a light-emitting particle will exceed beyond the size of a light detection region in a certain moving cycle time tcycle of the light detection region, it becomes difficult to obtain signals of the same light-emitting particle in the respective circulations of the light detection region. This is because, if the moving direction of a light-emitting particle once encompassed in the light detection region is incidentally along the passing region (predetermined route) of the light detection region, the light-emitting particle will be encompassed again in the light detection region after the circulation of the light detection region, but a light-emitting particle moves in the random direction, and thus, when the (average) displacement of the light-emitting particle during one circulation of the light detection region is so large to exceed beyond the size of light detection region, the possibility that the light-emitting particle, after once encompassed in the light detection region, deviates from the passing region of the light detection region and no longer be encompassed again in the light detection region after the circulation of light detection region is high. Thus, in order to catch periodic signals for achieving the computation of the above-mentioned diffusion constant D certainly, preferably, the moving cycle time tcycle of a light detection region is to be so adjusted that the (three dimensional) displacement 1 of a light-emitting particle in the moving cycle time tcycle of the light detection region will not exceed the diameter 2r of the light detection region as illustrated in FIG. 3D. Namely, when a diffusion constant is measured with the inventive method, preferably, the moving cycle time tcycle of a light detection region is adjusted in order that $$(2r)^2 > \delta \Delta t\text{cycle} \quad (6)$$

is satisfied (Here, ($\delta$ is the dimension, wherein $\delta=3$.). In this regard, in an actual measurement, the moving cycle time tcycle of a light detection region may be adjusted so that the conditions of the above-mentioned Expression (6) will be satisfied for the expected diffusion constant of a light-emitting particle to be tested.

Operation Processes

In the embodiment of the measuring method of a diffusion constant of a light-emitting particle in accordance with the present invention with the optical analysis device 1 as illustrated in FIG. 1A, concretely, there are conducted (1) a process of preparation of a sample solution containing light-emitting particles, (2) a process of measuring the light intensity of a sample solution and (3) a process of analyzing the measured light intensity. FIG. 4 shows the operation processes in this embodiment in the form of a flow chart.

(1) Preparation of a Sample Solution

The particle to be observed in the inventive method may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids.). Also, the particle to be observed may be a particle which emits light by itself, or may be a particle to which a light emitting label (a fluorescence molecule, a phosphorescence molecule, and a chemiluminescent or bioluminescent molecule) is attached in an arbitrary manner.

(2) Measurement of the Light Intensity of a Sample Solution

In the process of the measurement of the light intensity in the optical analysis in accordance with the scanning molecule counting method of this embodiment, there is performed measuring the light intensity with driving the mirror deflector 17 to move the position of the light detection region within the sample solution (to scan in the sample solution) (FIG. 4—step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, and the process of detecting light from the light detection region during the moving of the position of the light detection region) memorized in a storage device (not shown), and then illuminating the light detection region in the sample solution with the excitation light and measuring light intensity will be started. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetector 16 sequentially converts the detected light into an electric signal and transmits it to the computer 18, which generates the time series light intensity data from the transmitted signals and store it in an arbitrary manner. The photodetector 16 is typically a super high sensitive photodetector which can detect an arrival of a single photon, and thus the detection of light may be the photon counting performed in the manner of measuring sequentially the number of photons which arrive at the photodetector for every predetermined unit time (BIN TIME), for example, every 10 μs, during a predetermined time, and accordingly the time series light intensity data will be a time series photon count data.

Regarding the moving speed of the position of the light detection region, in the scanning molecule counting method, generally, in order to perform quantitatively precisely individual detection of a light-emitting particle to be observed from the measured time series light intensity data, preferably, the moving speed of the position of the light detection region during light intensity measurement is set to a value quicker than the moving speed in the random motion, i.e., the Brownian motion of a light-emitting particle. When the moving speed of the position of the light detection region is slower than the movement of a particle owing to the Brownian motion, the particle moves at random in the region as schematically drawn in FIG. 5A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data (When a light-emitting particle passes through the light detection region in an approximately straight line, the profile of the light intensity change is similar to the excitation light intensity distribution. See the upper row of FIG. 6A.) and the correspondence between each light-emitting particle and light intensity can be easily determined.

Concretely, the time $\Delta\tau$ required for a light-emitting particle having a diffusion coefficient D to pass through the light detection region of radius r (confocal volume) by the Brownian motion is given from Expression of the relation of mean-square displacement:

$$(2r)^2 = 6D \cdot \Delta\tau \tag{7}$$

as:

$$\Delta\tau = (2r)^2/6D \tag{8},$$

and thus, the velocity of the light-emitting particle moving by the Brownian motion (diffusional moving velocity) Vdif, becomes approximately $$V\text{dif} = 2r/\Delta\tau = 3D/r \tag{9}$$

Then, with reference to this, the moving speed of the position of the light detection region may be set to a value sufficiently quicker than Vdif. For example, when the diffusion coefficient of a light-emitting particle is expected to be about $D = 2.0 \times 10^{-10}$ m$^2$/s, Vdif will be $1.0 \times 10^{-3}$ m/s, supposing r is about 0.62 μm, and therefore, the moving speed of the position of the light detection region may be set to its approximate 10 times, 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

Furthermore, in the inventive method, as already described, preferably, the moving cycle time tcycle of a light detection region is set so that the condition of Expression (6) should be satisfied for the diffusion constant D of a light-emitting particle to be tested. For example, when the moving route of a light detection region is circular as illustrated in FIG. 3A, the relation among the moving cycle time tcycle, the moving speed v and the radius R of the moving route of the light detection region is given by:

$$2\pi R = v \cdot t\text{cycle} \tag{10},$$

and thus, from Expression (6), the moving speed v of the light detection region is set so that $$v > (3\pi R/r^2) \cdot D \tag{11}$$

will be established.

(3) Analysis of Light Intensity

When the time series light intensity data of a light-emitting particle in a sample solution is obtained by the above-mentioned processes, detection of a signal corresponding to light from a light-emitting particle on the light intensity data; extraction of signals of the same light-emitting particle and calculation of its diffusion constant may be performed in the computer 18 through processes in accordance with programs memorized in a storage device.

(i) Detection of a Signal Corresponding to a Light-Emitting Particle

Figure 5B:
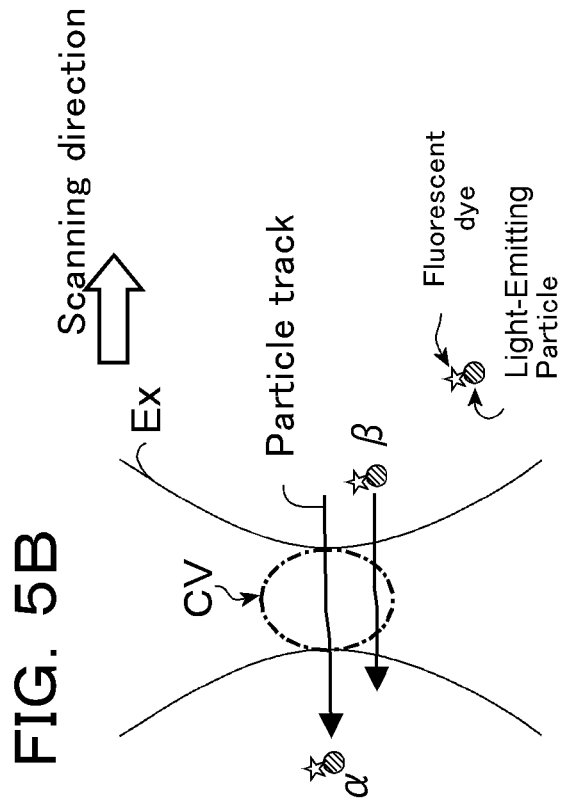
FIGS. 5A and 5B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle.
Figure 5A:
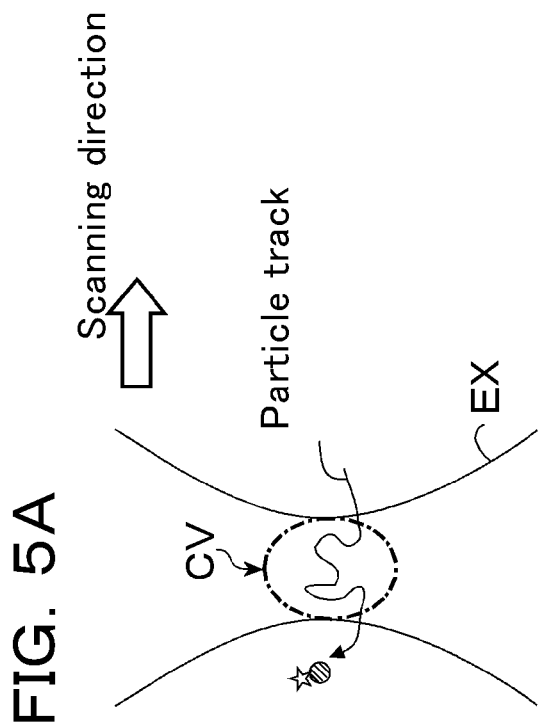

When the track of one light-emitting particle in its passing through the light detection region is approximately straight as shown in FIG. 5B, the light intensity variation in the signal corresponding to the particle to be observed in the time series light intensity data has a bell shaped profile reflecting the light intensity distribution in the light detection region (determined by the optical system) (See FIG. 8B). Thus, basically in the scanning molecule counting method, when the time width for which the light intensity exceeding an appropriately set threshold value continues is in a predetermined range, the signal having the profile of the light intensity may be judged to correspond to one particle having passed through the light detection region, and thereby one light-emitting particle is detected. And a signal whose time width for which the light intensity exceeding the threshold value Io continues is not in the predetermined range is judged as noise or a signal of a contaminant. Further, when the light intensity distribution in the light detection region can be assumed as Gaussian distribution:

$$I = A \cdot \exp(-2t^2/a^2) \tag{12},$$

and when the intensity A and the width a, computed by fitting Expression (12) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of operational methods of conducting collective detection of light-emitting particles from time series light intensity, a smoothing treatment is performed to the time series light signal data (FIG. 6A, the upper row "detected result (unsettled)") (FIG. 4—step 110, FIG. 6A mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method, etc. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 6A, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 6A, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically a Gauss function, it may be a Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 6B left, is judged as a signal corresponding to one light-emitting particle, and thereby, one light-emitting particle will be detected. On the other hand, a pulse signal, whose computed parameters of the bell-shaped function are not within the assumed ranges, as shown in FIG. 6B right, is disregarded as noise. The search and judgment of a pulse signal in the processes of the above-mentioned steps 130-150 may be repetitively carried out in the whole region of the time series light signal data (Step 160). Also, the process of detecting individually signals of light-emitting particles from time series light intensity data may be conducted by an arbitrary way other than the above-mentioned way.

(II) Extraction of Signals of the Same Light-Emitting Particle (FIG. 4—Step 170)

When the detection of pulse signals of light-emitting particles on the time series light intensity data has been done, the extraction of signals of the same light-emitting particle from those pulse signals will be conducted. As understood from the above-mentioned explanation, a signal of the same light-emitting particle appears continuously at each cycle time almost equal (not completely equal) to the moving cycle time of the light detection region. Then, the extraction of signals of the same light-emitting particle may be conducted by selecting a signal which appears continuously at each cycle time almost equal to the moving cycle time of the light detection region by an arbitrary way or algorithm. For example, in the simplest way, the signals of the same light-emitting particle may be extracted by an experimenter specifying a signal which appears continuously on the time series light intensity data at each cycle time almost equal to the moving cycle time of the light detection region by visual observation.

Moreover, as already noted, in the inventive method, for making it possible to capture periodic signals for making computation of the diffusion constant of a light-emitting particle significantly possible, preferably, the moving cycle time of the light detection region is adjusted (see Expression (6)) at a level that the (average) displacement of a light-emitting particle to be an observation object in each circulation of the light detection region does not exceed the size of the light detection region. In that case, the position of a once detected light-emitting particle after the circulation of the light detection region is expected to be within the size of the light detection region. Namely, after the detection of a signal of one certain light-emitting particle, a signal generated in the range centering at the time of the elapse of one cycle time of the light detection region and having a time width equal to a time for the light detection region to move its size (diameter d) in the moving direction:

$$\Delta T = d/v \quad (2)$$

can be judged as a signal of the same light-emitting particle as said one certain light-emitting particle. Thus, as one of extraction methods of signals of the same light-emitting particle, there may be employed an algorithm to judge a signal generated on time series light intensity data within the range of a time width $\Delta T$ centering at a time obtained by adding a cycle time of a light detection region to the generation time of one signal of a light-emitting particle as a signal of the same light-emitting particle as the light-emitting particle corresponding to said one signal. More concretely, as schematically illustrated in FIG. 7A, for example, after choosing signal $\alpha(i)$ of a certain light-emitting particle, when a signal $\alpha(ii)$ exists within the range of a time width $\Delta T$ centering at the time of elapse of one cycle time of the light detection region from the generation time of the selected signal $\alpha(i)$ (it may be the peak time.), the signal $\alpha(ii)$ is chosen as a signal of the same light-emitting particle as the signal $\alpha(i)$. After this, when a signal $\alpha(iii)$ exists within the range of a time width $\Delta T$ centering at the time of elapse of one cycle time of the light detection region (tcycle) from the generation time of the selected signal $\alpha(ii)$, the signal $\alpha(iii)$ is chosen as a signal of the same light-emitting particle as the already selected signals $\alpha(i)$ and $\alpha(ii)$. Accordingly, each time a signal is newly chosen, the process of choosing a signal which exists within the range of a time width $\Delta T$ centering at the time of elapse of one cycle time of the light detection region from the generation time of the selected signal is repeatedly performed, and thereby, it becomes possible to extract a series of signals (a signal group) of the same light-emitting particle on time series light intensity data. (In this regard, by rendering the generation time of the first selected signal to be the base point, each time of elapse of the moving cycle time (tcycle) of a light detection region, a signal which exists within the range of a time width $\Delta T$ centering on the time of the end of each cycle may be chosen as a signal of the same light-emitting particle as the first selected signal.)

Moreover, when two or more light-emitting particles enter into the passing region of a light detection region, as illustrated in FIG. 7A, between a certain group ($\alpha$) of signals appearing periodically, there will appear another group ($\beta$) of signals appearing periodically. In that case, for the other group of signals appearing periodically, signals may be extracted sequentially according to the same algorithm as the above. Namely, in a case that two or more groups of signals which appear periodically exist on one time series light intensity data, those signal groups may be extracted individually, respectively. In actual extracting processing, for example, in time series light intensity data, after choosing one certain signal ($\alpha(i)$) first and extracting a group of periodic signals in the above-mentioned manner with the one certain signal as the base point, one group ($\beta(ii)$, - - - ) of periodic signals is extracted with one signal ($\beta(i)$) not chosen as the extracted signal group as the base point, as noted above. Through repeating this process, two or more signal groups may be extracted on one time series light intensity data. The above-mentioned signal extraction method is advantageously used for automatic extraction with a computer especially in a case that signals of many light-emitting particles are detected on time series light intensity data.

(iii) Calculation of Displacement of a Light-Emitting Particle (FIG. 4—Step 180)

When the signal group of the same light-emitting particle has been extracted (for each light-emitting particle) as noted above, displacements of the light-emitting particle are estimated based on deviation times from the moving cycle time of the light detection region in the intervals of the generation times of the respective signals. As already noted, a displacement of a light-emitting particle in the time of k times circulations of a light detection region through a predetermined route (k-tcycle) is computed with Expression (4) using the deviation time from the time, k·tcycle, equal to k cycle time in the interval between the generation time of the first signal to and the generation time of the last signal tk in k times circulations of light detection region:

$$\Delta t = tk\text{-}to\text{-}k\text{-}t\text{cycle} \quad (13).$$

Thus, in the calculation of the displacements of a light-emitting particle, typically, for every combination of two signals among signals in the extracted signal group, the deviation time $\Delta t$ may be computed with Expression (13) and the displacement x of the light-emitting particle in the interval of the generation times of the respective signals may be computed by multiplying the computed $\Delta t$ by the moving speed v of the light detection region (Expression (4)). For example, as in FIG. 7B, supposing five approximately periodic signals are detected, the number of combinations of signals giving the deviation time (displacement of a particle) in one cycle, two cycles, three cycles and four cycles of the moving of a light detection region is 4 (1, 5, 8, 10), 3 (2, 6, 9), 2 (3, 7) and 1 (4), respectively, and thus, in total, ten data of the deviation time and displacement of the particle will be computed. And, when the number of signals in a signal group of a light-emitting particle is n, the data of a deviation time and a displacement of a particle are acquired for each of times equal to one to n−1 cycles, where the total number of data will be n (n−1)/2.

(iv) Computation of a Diffusion Constant (FIG. 4—Step 190)

Thus, when displacements of one light-emitting particle in the respective moving times of the light detection region (the number of circulations×the moving cycle time) have been computed through the process in the above-mentioned step 180, the diffusion constant D of the light-emitting particle is computed using the relation of Expression (5). For instance, in one manner, as schematically illustrated in FIG. 7C, a straight line is fit with the least square method, etc. to plots of square values $x^2$ of displacements in time (the number of circulations×the moving cycle time) of the particle obtained in step 180, and the diffusion constant D may be computed from the gradient of the straight line (=2D). (In the fitting of a line, the fitting of a straight line to square values $x^2$ of displacements of a particle (x in the diagram) or the fitting of a straight line to the averages of square values $x^2$ of displacements of a particle in the respective cycle times (● in the diagram) may be performed.). Further, for each of displacements x of a particle, there may be computed:

$$D = x^2 / (2k\text{·}t\text{cycle}) \quad (14)$$

and, the average of the computed Ds may be defined as the diffusion constant of the light-emitting particle.

Thus, according to the above-mentioned inventive method, in the scanning molecule counting method in which a light-emitting particle is detected individually by scanning a sample solution with a light detection region, it becomes possible "to measure" a diffusion constant of a light-emitting particle. As already described, the diffusion constant is a physical property reflecting the size and shape of a particle, and therefore, according to this invention, by attaching a light emitting label to an arbitrary particle to make it a light-emitting particle and measuring the diffusion constant of this light-emitting particle, it becomes possible to acquire the information about the size, structure or their change(s) of the particle wanted to observe, or various intermolecular interactions. Especially, in the present invention, the measurable magnitude of the diffusion constant can be changed by adjusting the moving cycle time of a light detection region, and therefore, it is expected that the diffusion constants of the comparatively wide range of kinds of particles are measurable. In an actual measurement, the moving cycle time of a light detection region may be adjusted to a suitable value through a preliminary experiment so that the periodic signals of a particle to be observed can be acquired.

In order to verify the validity of the present invention explained above, the experiments described below were conducted. In this regard, it should be understood that the following embodiments illustrate the validity of the present invention only, not intended to limit the scope of the present invention.

Embodiment 1

Measurement of Diffusion Constant of a Light-Emitting Particle

It was verified that the diffusion constant of a light-emitting particle was measured by the inventive method.

For a sample solution, there was prepared a solution in which plasmids (pBR322, Takara Bio, Inc., Cat. No. 3035) as particles to be observed were dissolved to be at 1 pM into a phosphate buffer (containing 0.05% Tween20) which included SYTOX Orange (Invitrogen Corp., Cat. No. S-11368) at 10 nM. In this connection, SYTOX Orange is a fluorescent dye which exhibits 500 times increase of fluorescence intensity when it binds with DNA (plasmid). In the light measurement, a single molecule fluorescence measuring apparatus MF20 (Olympus Corporation), equipped with the optical system of a confocal fluorescence microscope and a photon counting system, was used as the optical analysis device, and a time series light intensity data (photon count data) was acquired for the above-mentioned sample solution in accordance with the manner explained in the above-mentioned "(2) Measurement of the light intensity of a sample solution". In that time, a 633-nm laser light was used for excitation light, and, using a band pass filter, the light of the wavelength band of 660 to 710 nm, was measured, and a time series light intensity data was generated. The light detection region was made circulate a circular route (radius was about 23.9 μm.) with the moving cycle time of 10 msec. at 15 mm/second. And, BIN TIME was set to 10 μsec.: and the measurement time was set to 2 seconds. After the light intensity measurement, in accordance with the procedures described in the above-mentioned "(3) (i) Detection of a signal corresponding to a light-emitting particle", the smoothing treatment was applied to the time series light intensity data acquired with the sample solution, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. Then, only the pulse signal satisfying the following conditions:

20 μsec.<pulse width<400 μsec.

Peak intensity>1.0 [pc/10 μsec.]

Correlation coefficient>0.95 (A)

was judged as a signal corresponding to a light-emitting particle, while a pulse signal which did not satisfy the above-mentioned conditions was disregarded as noise.

FIG. 8A shows examples of signals 1-5, indicating light of a light-emitting particle, which appeared periodically at about 10 m seconds (which was the moving cycle of the light detection region) in the data of 1.5 to 1.6 seconds in the light intensity data obtained in the above-mentioned measurement for 2 seconds. With reference to the enlarged diagrams in the time direction, all the signal were of an almost bell shaped pulse form signal as shown in FIG. 8B. The peak time of each of the above-mentioned signals was as follows (the unit is m seconds).

| | |
|---|---|
| Signal 1 | 1510.741 |
| Signal 2 | 1520.726 |
| Signal 3 | 1530.738 |
| Signal 4 | 1540.767 |
| Signal 5 | 1550.825 |

Since the cycle time of the series of the signals was almost equal to the moving cycle time of the light detection region, it is thought that the signals were of the same light-emitting particle. Thus, using the peak times of the above-mentioned signals, in accordance with the way described in "(iii) Calculation of displacement of a light-emitting particle", there was calculated with Expression (13) the deviation time $\Delta t$ from the time equivalent to the moving cycle time in the interval of the generation times of the signals (the number of cycles×the moving cycle time) for each of the combinations of two of the five signals, and further, the displacements x of the light-emitting particle were computed with Expression (4). FIG. 8C is a diagram in which the square values ($x^2$) of the displacements x thus computed are plotted against time (the number of cycles x the moving cycle time) (Each point is the average of the square values of the displacements x in each time.). As understood from the diagram, the average of square values $x^2$ of the displacements x was almost proportional to the time. This shows that the relation between the average of square values $x^2$ of the displacements x and the time, expressed with Expression (5), was established, and thus, the displacements x of a light-emitting particle owing to the Brownian motion is computable based on the deviation time $\Delta t$ from time equivalent to the moving cycle time in the interval of the generation times of the above-mentioned signals. In this connection, the diffusion constant D obtained from the inclination (=2D) of the straight line having been obtained by fitting a straight line to the plots of FIG. 8C by the least square method was $3.89 \times 10^{-11}$ [$m^2$/s].

Further, all groups of signals corresponding to the same light-emitting particles were independently extracted from signals of light-emitting particles in the whole of the light intensity data (FIG. 9) obtained in the above-mentioned measurement for 2 seconds, and the diffusion constant was computed for each of the light-emitting particles. In the extraction of signals, as described in "(ii) Extraction of Signals of the Same Light-emitting Particle", after selecting a signal of one light-emitting particle first on the light intensity data, a signal which was present in the range of a time width $\Delta T$, given by Expression (2), centering at a time of the elapse of the moving cycle time (tcycle) of the light detection region from the peak generation time of the first selected signal, was selected as a signal of the same light-emitting particle as that of the first selected signal, and a group of signals was extracted by repeating the process of selecting a signal which was present in the range of a time width $\Delta T$, given by Expression (2), centering at a time of the elapse of the moving cycle time (tcycle) of the light detection region from the peak generation time of the newly selected signal. Subsequently, by repeating the process of extracting a group of periodic signals as noted above with rendering one signal, not chosen in the previous signal group, to be a base point, a plurality of signal groups were extracted on one time series light intensity data. In the example of FIG. 9, time $\Delta T$ given by Expression (2) was set to $\Delta T=53$ μsec. (calculated with d=0.8 μm and v=15 mm/sec.) In the result, while the total number of signals of light-emitting particles was 7188 on the light intensity data of FIG. 9, the number of the groups of signals periodically generated twice or more at the moving cycle time of the light detection region was 1708 (The total number of periodically generated signals was 4156.). This number of the groups of signals is equivalent to the number of light-emitting particles, and therefore, in the case of the present embodiment, the values of the diffusion constants of 1708 light-emitting particles were obtained in one light intensity data of the measurement for 2 seconds. Thus, for each of the 1708 sets of the detected signal groups, in accordance with Expression (13), deviation times $\Delta t$ from time equivalent to the moving cycle time in the intervals of the generation times of signals were computed, and after that, using the relation of Expression (5) with square values $x^2$ of the displacements x, computed from $\Delta t$ according to Expression (4), and the moving time of the light detection region (the number of the cycles x the moving cycle time), the diffusion constants were computed to be $9.9 \times 10^{-12}$ [$m^2$/s] in average.

The diffusion constant of a particle to be observed obtained by performing a measurement (with a single molecule fluorescence measuring apparatus MF-20) by FCS for a solution containing the above-mentioned particle to be observed (plasmid pbr322) in 10 nM was $4.0 \times 10^{-12}$ [$m^2$/s]. Also, supposing the specific volume of the particle to be observed is to be 1.0 $cm^3$/g and the particle to be observed is spherical, the diffusion constant computed theoretically with the Stokes Einstein equation (D=κBT/6πηr) becomes $2.2 \times 10^{-11}$ [$m^2$/s], and supposing the particle to be observed is cylindrical (4 nm in diameter, 680 nm in length are assumed), the theoretically computed diffusion constant becomes $4.2 \times 10^{-12}$ [$m^2$/s]. (Correction by Expression (8) in the nonpatent document 6 was used.). Therefore, the order of the result value of the diffusion constant in the above-mentioned present embodiment is almost equal to those of the FCS method and the theoretical value, and this shows that the measurement of the diffusion constant of a particle is possible by the inventive method.

Thus, as understood from the result of the above-mentioned embodiment, according to the above-mentioned inventive method, the measurement of the diffusion constant of a light-emitting particle is achievable in the scanning molecule counting method. Especially, the inventive method is designed to detect periodically generated signals of a light-emitting particle on light intensity data individually and compute the diffusion constant based on the generation times of the signals, and therefore, according to the inventive method, even when a light-emitting particle concentration in a sample solution is lower than the concentration range requested in optical analysis techniques, such as FCS, the measurement of the diffusion constant of a light-emitting particle is possible, and this feature will be advantageous in a case of performing an analysis of a rare or expensive sample often used in the field of research and development of Medicine and Biology. Moreover, in the inventive method, a diffusion constant is computed based on the generation times of periodically generated signals of a light-emitting particle on one-dimensional light intensity data, and thus, the load in computing is comparatively low, so that it is expected that the operation amount or time taken in calculation of the diffusion constant of one light-emitting particle is reduced as compared with the way of using image processing, such as SMT.

Further, although the example of measuring a diffusion constant using the scanning molecule counting method is explained in detail in the above, it should be understood that a diffusion characteristic value other than the diffusion constant is computable based on the deviation times from the moving cycle time of the light detection region in the intervals of the generation times of signals, and such a case also belong to the scope of the present invention. For example, an inclination of plots of square values of displacements of a particle against the time or a translational diffusion time computed based on "the deviation time from the moving cycle of the light detection region in the interval of the generation time of a signal" may be computed to be used for estimation of the size or structural change of a particle or an intermolecular interaction.

The invention claimed is:

1. A method of measuring a diffusion characteristic value of a light-emitting particle dispersed and moving at random in a sample solution using an optical system of a confocal microscope or a multiphoton microscope comprising steps of:
   moving periodically along a predetermined route a position of a light detection region of the optical system in the sample solution by changing an optical path of the optical system;
   measuring light intensity from the light detection region with moving the position of the light detection region in the sample solution to generate light intensity data;
   individually detecting a signal indicating light of a light-emitting particle on the light intensity data;
   extracting two or more signals corresponding to a same light-emitting particle among the detected signals indicating light of the light-emitting particle; and
   computing, using a computer, a diffusion characteristic value of the light-emitting particle corresponding to the extracted signals based on a deviation time from a moving cycle time of the light detection region in an interval of generation times of the extracted signals.

2. The method of claim 1, wherein, in the step of computing the diffusion characteristic value, the diffusion characteristic value is computed based on a displacement of the light-emitting particle corresponding to the extracted signals computed from the deviation times from the moving cycle time of the light detection region in the interval of the generation times of the extracted signal and a moving speed of the light detection region.

3. The method of claim 1, wherein the interval of the generation times of the extracted signal is a time difference of the generation times of any two signals in two or more continuous extracted signals.

4. The method of claim 1, wherein, in the step of extracting two or more signals corresponding to the same light-emitting particle, a signal generated in a time width determined based on a size and a moving speed of the light detection region and centering at a time given by adding a cycle time of the light detection region to a generation time of one signal in the signals indicating light of the light-emitting particle is judged to be a signal of the same light-emitting particle as the light-emitting particle corresponding to the one signal.

5. The method of claim 1, wherein, when signals indicating light from two or more light-emitting particles are present on the light intensity data, the diffusion characteristic value is independently computed for each of the two or more light-emitting particles.

6. The method according to any one of claims 1 to 5, wherein the diffusion characteristic value is a diffusion constant.

7. The method of claim 1, wherein the position of the light detection region is moved at velocity quicker than a diffusion moving velocity of the light-emitting particle in the sample solution.

* * * * *